(12) United States Patent
Panattoni et al.

(10) Patent No.: US 9,234,874 B2
(45) Date of Patent: Jan. 12, 2016

(54) DIMENSIONAL STABILIZATION OF SLAB GEL CASSETTES TO PREVENT DISTORTION CAUSED BY SWELLING GELS

(75) Inventors: Cory Panattoni, Winters, CA (US); Matthew Latham, Dixon, CA (US); Kara Kimmel, Richmond, CA (US); John Walker, San Leandro, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 630 days.

(21) Appl. No.: 13/371,667

(22) Filed: Feb. 13, 2012

(65) Prior Publication Data

US 2013/0056909 A1 Mar. 7, 2013

Related U.S. Application Data (60) Provisional application No. 61/588,830, filed on Jan. 20, 2012, provisional application No. 61/446,347, filed on Feb. 24, 2011.

(51) Int. Cl.
*B29C 39/26* (2006.01)
*G01N 27/447* (2006.01)
*B29C 39/02* (2006.01)

(52) U.S. Cl.
CPC .......... *G01N 27/44704* (2013.01); *B29C 39/02* (2013.01); *G01N 27/44756* (2013.01)

(58) Field of Classification Search
CPC .............. G01N 27/26; G01N 27/447; G01N 27/44704; G01N 27/44756; G01N 27/44743; B29C 39/02; B29C 39/026

USPC ......... 249/85, 94–96, 99, 101, 157, 160, 163, 249/164, 168, 169; 204/465–467, 606, 616, 204/619, 620; 264/331.11; 425/450.1
See application file for complete search history.

(56) References Cited

U.S. PATENT DOCUMENTS

| | | | |
|---|---|---|---|
| 3,842,020 A | 10/1974 | Garrett | |
| 3,881,683 A * | 5/1975 | Whitney | ...................... 249/117 |

(Continued)

FOREIGN PATENT DOCUMENTS

| | | | |
|---|---|---|---|
| GB | 2181248 A | 4/1987 | |
| JP | 63085348 A * | 4/1988 | ............. G01N 27/26 |

(Continued)

OTHER PUBLICATIONS

International Search Report and Written Opinion for PCT/US12/26557, dated Jun. 4, 2012, 16 pages.

(Continued)

*Primary Examiner* — Yogendra Gupta
*Assistant Examiner* — Kimberly A Stewart
(74) *Attorney, Agent, or Firm* — Kilpatrick Townsend & Stockton LLP (57) ABSTRACT

Slab gel cassettes for use in electrophoretic analyzes of biologically-derived mixtures are equipped with features that prevent the plastic walls of the cassettes from bowing outward when gels retained within the cassettes swell, as gels typically do during casting, storage, or both. In certain embodiments, these features are incorporated into, or mate with, the comb-shaped inserts that form the sample wells as the gels are being cast. In other embodiments, these features are complementary features incorporated into both the comb and the cassette.

5 Claims, 7 Drawing Sheets

(56) References Cited

U.S. PATENT DOCUMENTS

| | | | |
|---|---|---|---|
| 4,279,401 A * | 7/1981 | Ramirez et al. | 249/139 |
| 4,522,768 A * | 6/1985 | Roscrow et al. | 264/2.2 |
| 4,560,459 A * | 12/1985 | Hoefer | 204/467 |
| 5,073,246 A * | 12/1991 | Chu et al. | 204/619 |
| 5,284,565 A * | 2/1994 | Chu et al. | 204/619 |
| 5,384,025 A * | 1/1995 | Blasband | 204/619 |
| 5,433,837 A * | 7/1995 | Brunk et al. | 204/620 |
| 5,514,255 A * | 5/1996 | Gautsch | 264/104 |
| 5,543,097 A * | 8/1996 | Fang | 264/102 |
| 5,618,399 A * | 4/1997 | Gautsch et al. | 204/620 |
| 5,656,145 A * | 8/1997 | Nguyen et al. | 204/618 |
| 5,753,095 A | 5/1998 | Alpenfels et al. | |
| 5,809,625 A * | 9/1998 | Young et al. | 27/32 |
| 5,843,295 A * | 12/1998 | Steiner et al. | 204/619 |
| 5,989,403 A * | 11/1999 | Provonchee | 204/619 |
| 5,993,628 A * | 11/1999 | Selby et al. | 204/470 |
| 6,093,301 A * | 7/2000 | Van Atta | 204/617 |
| 6,123,219 A | 9/2000 | Cornell et al. | |
| 6,231,741 B1 * | 5/2001 | Tuurenhout et al. | 204/618 |
| 6,969,455 B1 * | 11/2005 | Helfer et al. | 204/618 |
| 7,135,101 B2 * | 11/2006 | Atchison et al. | 204/467 |
| 7,588,673 B2 * | 9/2009 | Latham | 204/616 |
| 7,749,367 B2 * | 7/2010 | Zhou | 204/467 |
| 2003/0141190 A1 * | 7/2003 | Alpenfels et al. | 204/606 |
| 2006/0163067 A1 | 7/2006 | Sevigny et al. | |
| 2006/0237317 A1 | 10/2006 | Perez et al. | |
| 2007/0056854 A1 * | 3/2007 | Latham | 204/606 |
| 2009/0049719 A1 | 2/2009 | Compton et al. | |
| 2011/0042217 A1 * | 2/2011 | Updyke et al. | 204/620 |
| 2011/0084194 A1 * | 4/2011 | Sevigny et al. | 249/160 |
| 2014/0138249 A1 * | 5/2014 | Wang et al. | 204/620 |

FOREIGN PATENT DOCUMENTS

| | | | | |
|---|---|---|---|---|
| JP | 04231490 A * | 8/1992 | | C25B 9/00 |
| JP | 2005062075 A * | 3/2005 | | G01N 24/477 |
| WO | 01/81910 A1 | 11/2001 | | |
| WO | 2005/098408 A1 | 10/2005 | | |
| WO | WO 2005095940 A1 * | 10/2005 | | G01N 27/44704 |

OTHER PUBLICATIONS

Supplementary European Search Report from EP 12750095.5, dated Oct. 22, 2014.

* cited by examiner

DIMENSIONAL STABILIZATION OF SLAB GEL CASSETTES TO PREVENT DISTORTION CAUSED BY SWELLING GELS

CROSS-REFERENCE TO RELATED APPLICATIONS

This application claims the benefit of U.S. Provisional Patent Application No. 61/446,347, filed Feb. 24, 2011, U.S. Provisional Patent Application No. 61/588,830, filed Jan. 20, 2012. The contents of both such provisional applications are incorporated herein by reference in their entirety.

BACKGROUND OF THE INVENTION

1. Field of the Invention

This invention resides in the field of electrophoresis performed in slab gels. In particular, this invention relates to slab gel cassettes in which the slab gels are retained in enclosures and often stored in buffer solutions until ready for use.

2. Description of the Prior Art

When a slab gel and the cassette (i.e., the flat-plate enclosure) in which it is cast are immersed in a buffer solution for packaging or storage purposes, the gel tends to absorb water from the buffer solution over time. This uptake of water causes swelling of the gel, and the swelling causes the gel to exert pressure on the plates of the cassette. The pressure causes the plates to bow outward, with the pore size of the gel becoming greater at the center of the gel compared to the edges. When samples are loaded onto the gel and electrophoresis is performed, this variation in pore size causes the solute bands from the sample to migrate faster at their centers, producing an effect on the shapes of the bands known as a "smiling" effect, which increases as the bands migrate greater distances through the gel. This makes reading of the gels difficult and lowers reproducibility and accuracy.

Cassettes that are particularly susceptible to distortion are those in which one or both of the flat plates is made of plastic, and often plastic that is approximately 2.0 mm or less in thickness. While cassettes are available in which one or both plates are made of glass, cassettes in which both plates are plastic offer certain advantages, including ease of manufacture of the plates themselves and ease of sealing the plates to each other along their edges, typically by sonic welding, with appropriate spacers to fix the thickness of the cavity. Electrophoresis "cells" in which the cassettes are placed and that contain electrodes and appropriate electrical connections for imposing an electrical potential along the lengths of the gels are often designed for cassettes of particular sizes which impose an upper limit on the thickness of the cassette walls. Many cassettes are susceptible to distortion for this reason as well.

Another problem that arises in slab gel cassettes is one involving the formation of wells along the upper edge of the gel that are used for the loading of samples onto the gel. These wells are formed by the use of a well-forming insert commonly known as a "comb," which is a bar with dentiform projections, or "teeth," along one longitudinal edge of the bar. The comb is placed on the cassette prior to the casting (polymerization) of the gel with the teeth extending into the cavity to form the wells as the polymerization reaction proceeds. Ideally, the thickness of each of the teeth is equal to the gap width between the flat plates of the gel, so that the final gel will extend upwards between adjacent teeth but not into regions between the fronts or backs of individual teeth and the cassette walls where gel material can make it difficult to remove the comb from the cassette and expose the wells. In practical usage, however, avoidance of gel material in these regions is difficult to achieve, and is more so when these regions widen. The comb is also typically made of a material that inhibits polymerization at its surface, thereby preventing the polymerized gel from adhering to the comb. This is of value since adhesion of the gel makes it difficult to remove the comb without damaging the partitions in the gel that separate the wells. The comb material also inhibits polymerization in the spaces between the teeth of the comb and the cassette plates, but tends to lose its ability to do this when these spaces widen or when combs are used that are off-specification or otherwise thinner than expected. Polymerization in these spaces can also occur when too much polymerization catalyst is present or when copper is present in the monomer solution at a high concentration. The formation of gel material in these spaces is known as "webbing," and interferes with the loading of the samples.

Disclosures of combs designed for use in the casting of electrophoresis gels appear in the following United States patents: Sugimoto et al. (Fuji Photo Film Co., Ltd.) U.S. Pat. No. 4,883,577, Nov. 28, 1989; Bambeck et al. U.S. Pat. No. 4,909,918, Mar. 20, 1990; Chu et al. (Bio-Rad Laboratories, Inc.) U.S. Pat. No. 5,073,246, Dec. 17, 1991; Bettencourt et al. (Bio-Rad Laboratories, Inc.) U.S. Pat. No. 5,164,065, Nov. 17, 1992; Chu et al. (Bio-Rad Laboratories, Inc.) U.S. Pat. No. 5,284,565, Feb. 8, 1994; Steiner et al. (Pharmacia Biotech) U.S. Pat. No. 5,843,295, Dec. 1, 1998; Selby et al. (The Perkin-Elmer Corporation) U.S. Pat. No. 5,993,628 (Nov. 30, 1999); Scott (C. B. S. Scientific Co., Inc.) U.S. Pat. No. 6,139,709, Oct. 31, 2000; Latham (Bio-Rad Laboratories, Inc.) U.S. Pat. No. 7,588,673 B2, Sep. 15, 2009; and Perez et al. (Bio-Rad Laboratories, Inc.) U.S. Pat. No. 7,658,827 B2, Feb. 9, 2010.

SUMMARY OF THE DISCLOSURE

Methods and structures for addressing the various problems enumerated above are described below. The slab gels in these descriptions are retained in a slab-shaped cavity inside a plastic-walled gel enclosure, referred to in the industry as a "cassette." The cavity has at least one open side through which a monomer solution from which the gel will be cast can be introduced. The structure of the enclosure, or of parts that are either joined to the enclosure or otherwise used in conjunction with the enclosure, help impose a maximum dimension on the width of the cavity, i.e., the gap width between the two plastic plates, during gel casting and storage. When in storage, the gel and cassette are typically maintained in contact with a storage buffer, which exacerbates the swelling problem. By imposing a maximum dimension on the cavity width, the tendencies of the cavity to expand due to pressure generated inside the cavity by swelling of the gel are offset, and the gap width between the plates is inhibited or prevented entirely from increasing. The structural feature or features that achieve this result can reside either in the plastic plates themselves, in the comb, in both the plates and the comb, or in additional components that are attached onto or generally used in conjunction with either the plates or the comb. An alternative means of achieving dimensional stability is by lowering the pressure inside the gel cavity once the monomer solution has been placed inside the cavity or soon after the gel has been cast, and maintaining the reduced pressure level until a short period of time before the cassette is used in an electrophoresis experiment.

Included among the variety of structural features disclosed herein to offset the swelling of the gel and thereby prevent outward bowing of the cassette plates are removable attachments to the cassette or to the comb used in conjunction with the cassette, features (removable or otherwise) that secure the gap width along the upper edge of the gel where samples are introduced and where the sample wells reside, and features (removable or otherwise) that secure the gap width along the lower edge of the gel, which is in the downstream direction of the migration of the sample solutes during electrophoresis.

For those embodiments of the invention that entail the use of a comb, a comb is disclosed herein that, in addition to serving its function of forming a row of sample wells in an electrophoresis gel within the cassette, also prevents outward bowing of the cassette plates when the tendency of the gel to swell causes pressure to be exerted against the plates. In addition to its teeth, the comb in certain embodiments of the invention has hook-like projections extending from both its front and back surfaces that engage the two plates, respectively, of the cassette, at the upper edges of the plates. These projections prevent the plates from bowing out at these edges and at the areas adjacent to these edges. The hook-like projections can have hook-shaped profiles or any other shape or profile, such as flat tabs, for example, that will engage the plates and help them resist bowing. The comb can contain as few as one hook-like projection on each side, or two or more on either side. Best results will generally be achieved when the projections engage the centers of the upper edges of the plates, or locations along the upper edges on both sides of the centers in a symmetrical arrangement around the centerline of each plate. A single projection on each side that is wide enough to secure a portion of the length of the upper edge of the plate on that side can be used, or two or more projections can be included on a given side of the comb, sufficiently spaced apart to produce support along the width of the plate. A plurality of projections on either side of the comb, evenly spaced along the comb will provide still greater assurance that the cassette plates remain parallel and are restrained from bowing. In certain embodiments of the design, other features are included to accommodate particular cassettes. For cassettes with plates of unequal height, for example, the hook-like projection(s) on one side of the comb will be higher than the hook-like projection(s) on the other side to match the different heights of the cassette plates.

In certain other embodiments of the invention, the comb and cassette have interlocking features on their surfaces that are readily engaged and disengaged by simply inserting and removing the comb. The interlock can be achieved by the profiles of the features, such as for example, tabs, knobs, or ridges on one surface and complementary grooves on the other, each the profiles such that the features are engaged either by pressing or snapping together or by sliding one inside the other.

Other features and variations will be apparent to those of skill in the art, and some are shown and described below.

DETAILED DESCRIPTION OF SELECTED EMBODIMENTS

While the devices and methods covered by the claims herein are susceptible of a wide range of embodiments and implementations, a full understanding of the invention as a whole will be readily gained from descriptions of specific embodiments. Several such embodiments are described below, and certain of these are illustrated in the Figures.

Figure 1:
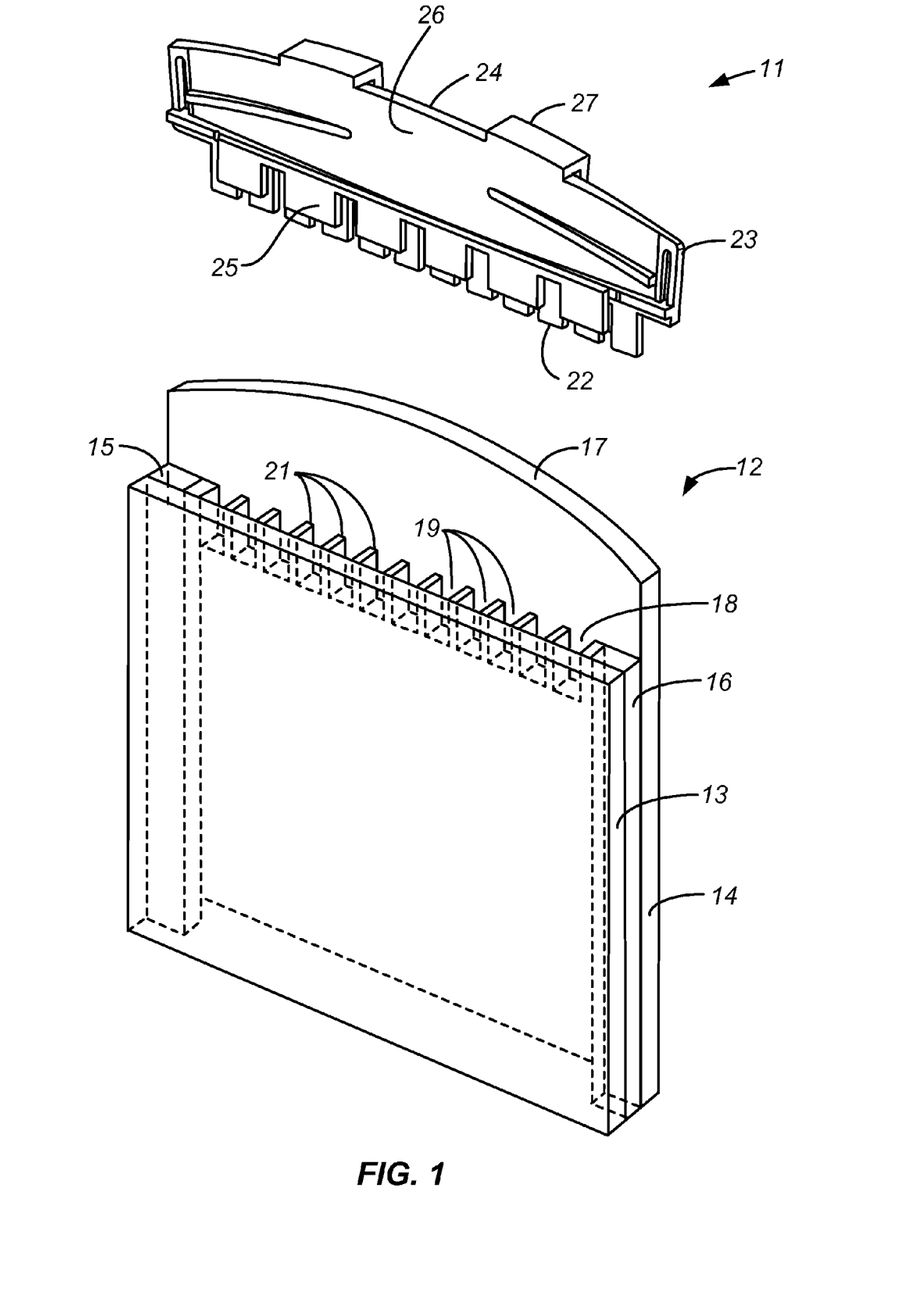
FIG. 1 is a perspective view of a combination of a comb and a slab gel cassette as an illustration of one embodiment of the present invention, separated from each other to expose the contacting parts.

As noted above, one such embodiment is a comb of specialized construction to include features for engaging the upper edges of the plastic plates of the cassette. FIG. 1 depicts such a comb 11 poised above a slab gel cassette 12 from which the comb has been removed following the casting of a gel in the cassette. Both the comb 11 and the cassette 12 are oriented vertically, as they will be during use. The cassette 12 is formed from two flat plates, one of which is a front plate 13 and the other a back plate 14, sealed and spaced apart at their two side edges by spacers 15, 16. Both the spacers and the methods for joining the plates and sealing them along these edges are known in the art and conventional to cassettes and slab gel enclosures in general. The spacers 15, 16 set a gap between the two plates, the gap forming the gel cavity, and the upper and lower borders of the cavity are open for exposure of the top and bottom edges of the gel to a cathode and anode, respectively through upper and lower buffer solutions. The back plate 14 is taller than the front plate 13, as is common among slab gel cassettes to facilitate the retention of an upper buffer solution in contact with the upper edge of the gel. The upper edge 17 of the back plate is arched while the upper edge 18 of the front plate is straight and horizontal. The gel is shown in dashed lines and contains a series of rectangular indentations 19 along its upper edge serving as sample wells, adjacent wells being separated by partitions 21 which are cast as part of the gel. In the conventional manner, the sample wells are formed by the teeth 22 on the comb 11. The number of teeth shown, and hence the number of sample wells, is twelve, but this is only an example; the number can vary widely.

Figure 2:
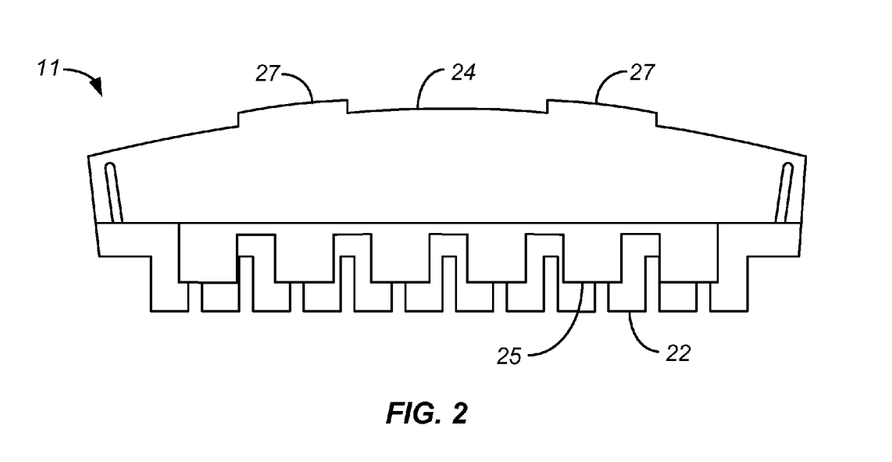
FIG. 2 is a front view of the comb of FIG. 1.
Figure 3:
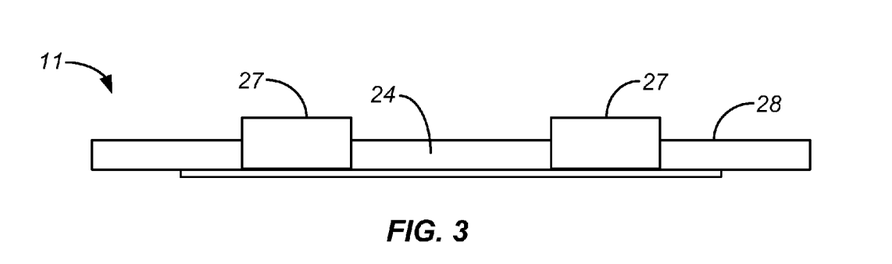
FIG. 3 is a top view of the comb of FIG. 1.

The comb 11 is a bar 23 with an arched upper edge 24 to match the arched upper edge 17 of the back plate 14 of the cassette. A row of six tabs 25 extends forward from, parallel to, and uniformly spaced from, the forward face 26 of the bar to serve as the forward hook-like projections. Similarly, two tabs 27 extend rearward from, parallel to, and uniformly spaced from, the rear face (not visible) of the bar to serve as the rear hook-like projections. The comb is also shown in a front view in FIG. 2 and in a top view in FIG. 3. The rear face 28 is indicated in FIG. 3.

Figure 4:
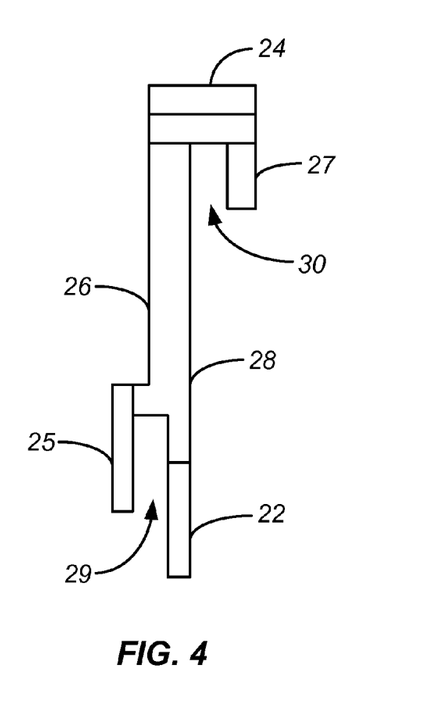
FIG. 4 is an end view of the comb of FIG. 1.
Figure 5:
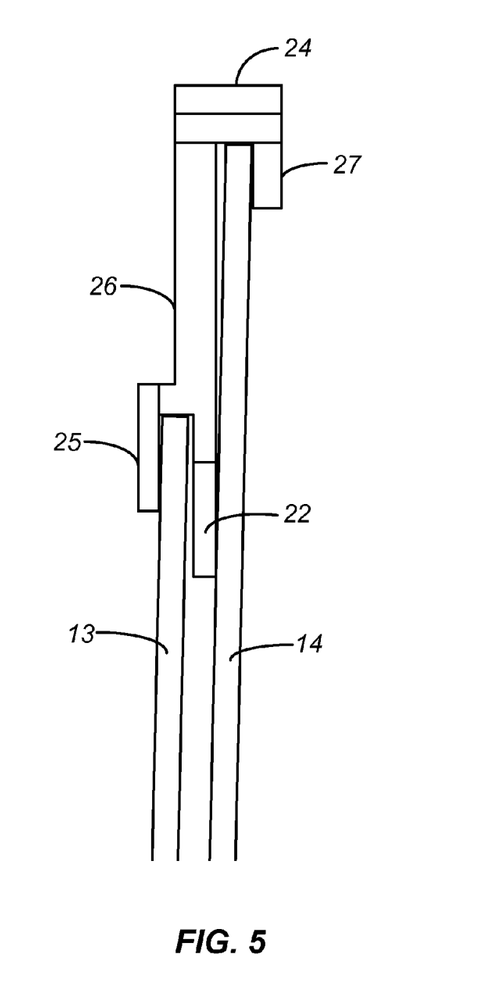
FIG. 5 is the same view of the comb as FIG. 4 but shown in position over the front and back plates of the cassette.

An end view of the comb is shown in FIG. 4. The difference in height between the forward tabs 25 and the rear tabs 27 is more clearly visible in FIG. 4. Each of the eight tabs is flat and parallel to the forward face 26 and rear face 27 of the comb. The tabs thus leave gaps 29, 30 to accommodate the two plates of the cassette. FIG. 5 shows the comb in place on the cassette, with the front plate 13 and the back plate 14 indicated.

Figure 6:
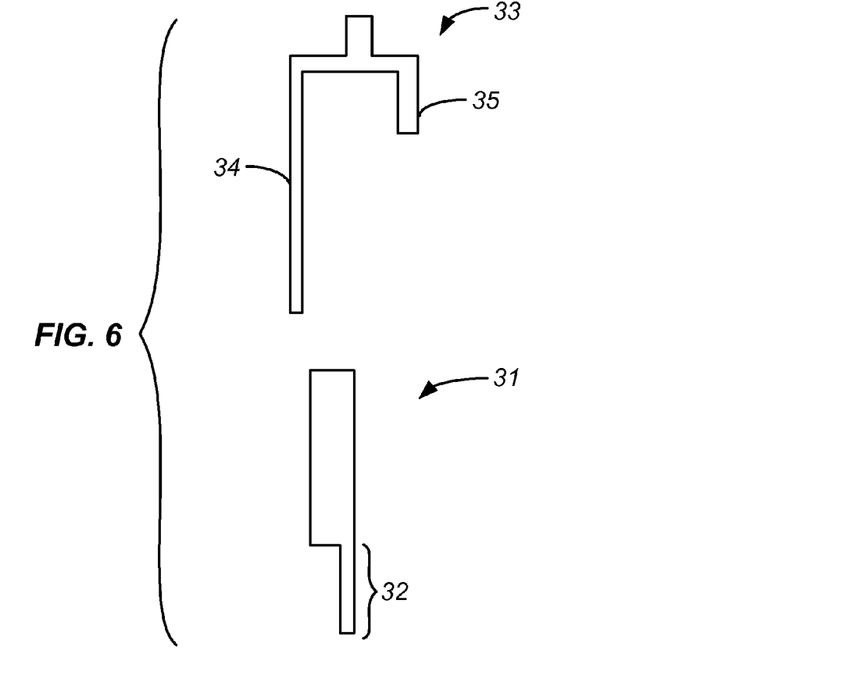
FIG. 6 is an end view of a comb and attachment that together serve as an alternative to the comb of FIG. 1.
Figure 7:
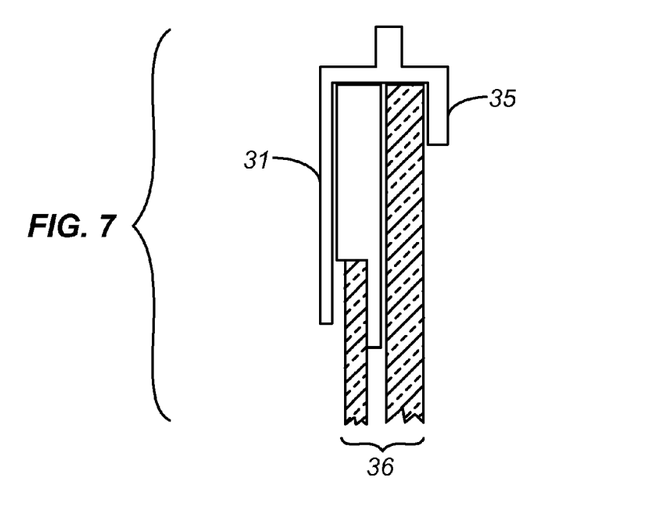
FIG. 7 is an end view of the comb and attachment of FIG. 6 in place on a cassette.

A variation on the comb of FIGS. 1 through 5 is shown in FIGS. 6 and 7. In this variation, the comb and hooks combination is divided into two parts, shown separately in FIG. 6 and together in FIG. 7 where they are also shown in place on a cassette. The comb itself 31 with its downwardly extending teeth 32 constitutes the first part, and an attachment 33 that contains the forward tabs 34 and the rear tabs 35 constitute the second part. The attachment 33 rests on the top of the comb 31, with the tabs 34, 35 extending down the front and rear faces of the corn, the tabs 34, 35 being spaced widely enough apart to accommodate both the comb and the cassette. The comb 31, attachment 33, and the upper edge of the cassette 36 are shown assembled in FIG. 7.

The comb can be made of moldable or machinable materials, examples of which are polycarbonate, acrylic, and polytetrafluoroethylene. The gaps 29, 30 are sized to form a close but loose fit, rather than a friction fit. The appropriate fit will be sufficiently loose to allow manual placement of the tabs over the upper edges of the plates 13, 14 and removal of the comb once the gel is cast. The fit is a sufficiently close one however to prevent and significant bowing of the plates upon pressure from a swelling gel.

Figure 8:
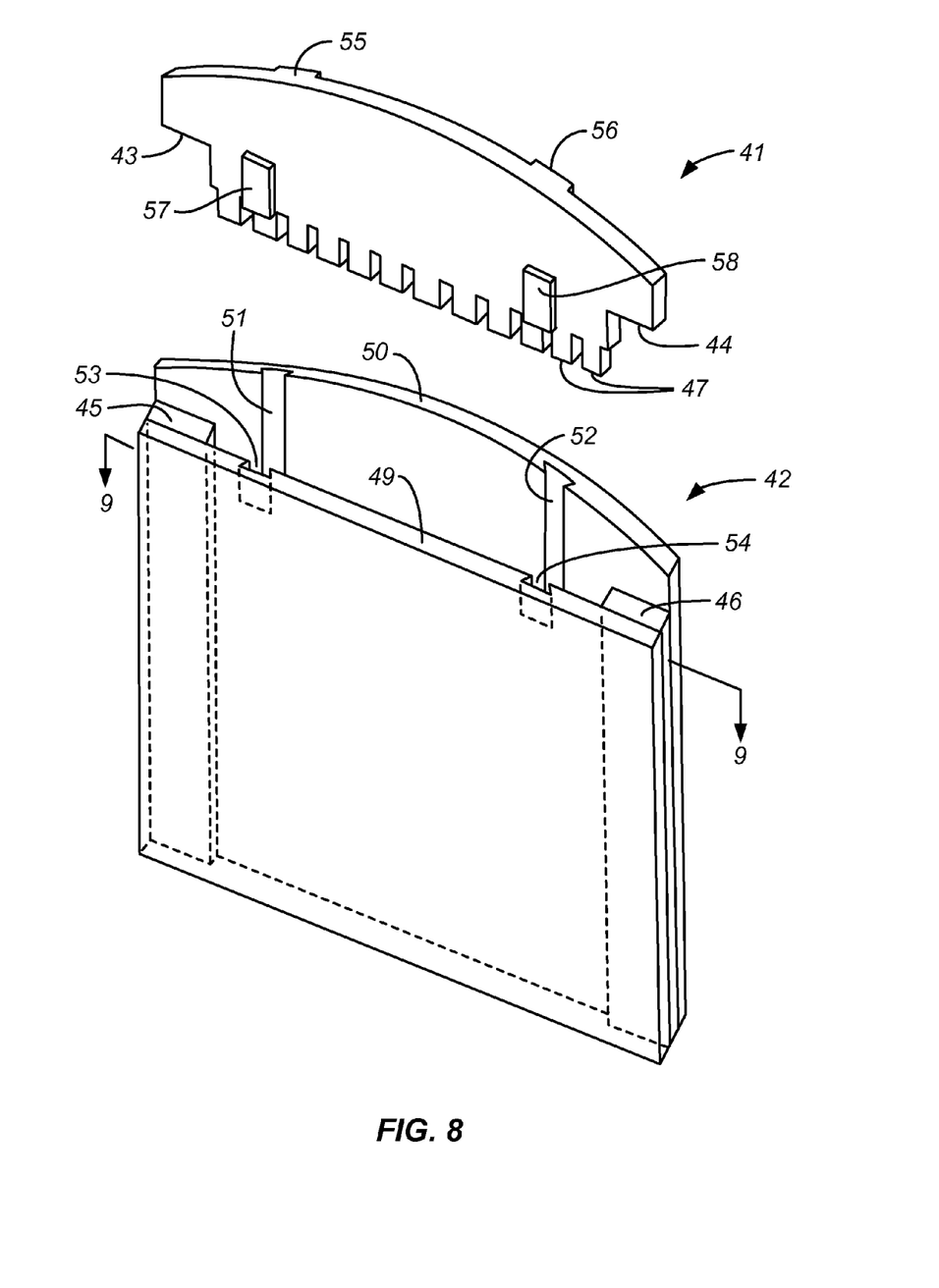
FIG. 8 is a perspective view of a combination of a comb and a slab gel cassette, different from those of the preceding figures, as an illustration of a further embodiment of the present invention. The comb and cassette are separated from each other to expose the contacting parts.
Figure 9:
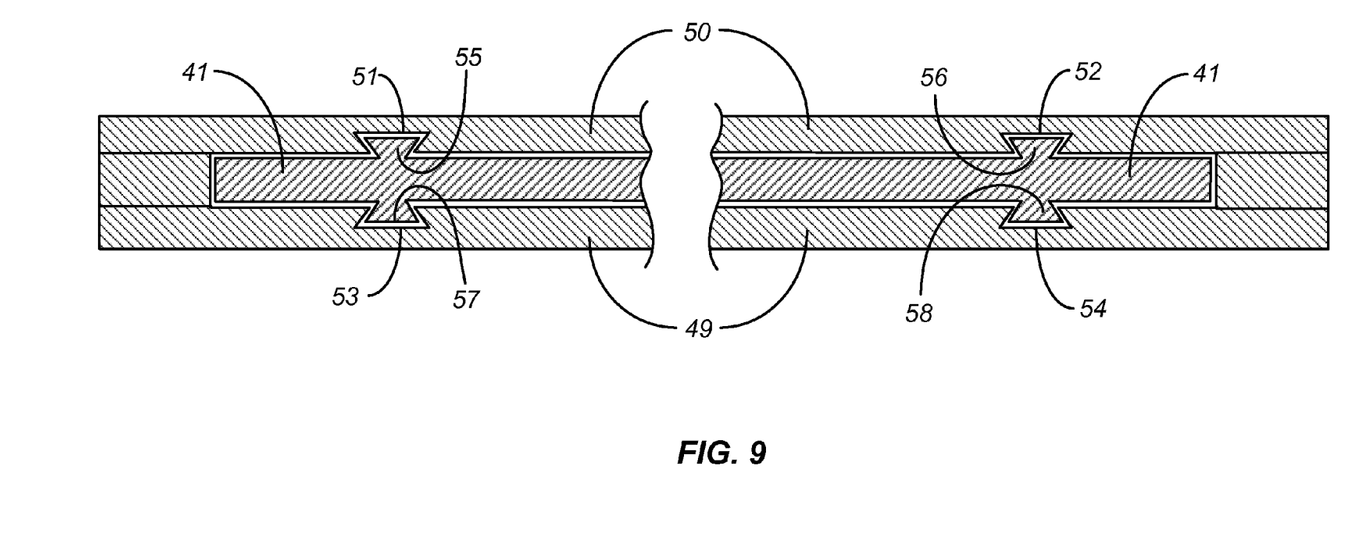
FIG. 9 is a cross section view of the comb and cassette of FIG. 8, along the line 9-9 of FIG. 8.

A further alternative to the comb and cassette combination of the preceding figures is that shown in FIGS. 8 and 9. FIG. 8, like FIG. 1, depicts a comb 41 posed above a slab gel cassette 42 into which the comb will be lowered before the gel-forming solution has been polymerized into a gel. The outer edges 43, 44 of the comb are shaped to rest on the lateral sides of the cassette 42, and specifically in this case on the upper ends 45, 46 of the spacers, while the teeth 47 of the comb extend into the gel cavity between the spacers and the front and back plates 49, 50. The front and back plates each have grooves 51, 52, 53, 54 on their inward-facing surfaces, and the comb 41 has ridges 55, 56, 57, 58 whose cross sections have profiles that are complementary to the grooves 51, 52, 53, 54 and whose locations on the comb surface directly face the locations of the grooves. As the comb is lowered onto the cassette, the ridges will slide into and along the grooves, and the teeth 47 will extend below the ridges and grooves. The result is a tongue-and-groove construction with undercuts to prevent the tongue from leaving the groove other than by sliding out of the open end of the groove. The ridges and grooves terminate at a level above the teeth, thereby allowing the gel being cast in the cavity to have flat forward and rear surfaces. As shown in the cross section of FIG. 9, the ridges and grooves have trapezoidal profiles, causing them to interlock and thereby fix the distance between the forward and rear plates 49, 50 of the cassette, and preventing these plates from bowing outward along their top edges as the gel between them swells.

While two ridges (or tongues with undercut) are placed on each surface of the comb, with the corresponding grooves occupying complementary positions on the plates of the cassette, the number and placement can vary and are not critical provided that they prevent the plates from bowing outward. A single ridge on each side of the comb and a single correspondingly placed groove on each plate of the cassette can achieve a similar result, as can three or more paired ridges and grooves on each side. Nor is the same number required on both sides. As a further alternative, the ridge or other protrusion can be on the cassette plates and the grooves on the comb. The trapezoidal profiles can also be replaced by any other profiles that have serve an interlocking function. Interlocking profiles in general will be readily apparent to those of skill in the art.

Other options for preventing outward bowing of the plastic plates are those residing in the construction of the plates themselves. One such option is to use a composite material that is more rigid than the plastic conventionally used. The plastic most commonly used in the prior art is polycarbonate, and as noted above, one or both of these plates are typically less than 2.0 mm, most commonly about 1.8 mm to about 1.9 mm, in thickness per plate. Greater rigidity can be achieved by using plates that are substantially thicker, such as for example about 3.0 mm or greater, or from about 3.0 mm to about 10.0 mm, or from about 3.0 mm to about 5.0 mm. Another option is to use a reinforced plastic, such as a glass-filled plastic. Glass-filled polycarbonate sheets containing from about 10% to about 30% glass are examples, the sheet thicknesses being somewhat greater, such as by 1.0 mm to 3.00 mm or more, than those of cassettes formed of non-filled plastic. A third option is to use plastic plates that are ribbed for structural reinforcement. A rib on the outside surface of the plate, preferably a rib running parallel to the open edge of the cassette cavity, can lessen or eliminate any tendency of the plate to bow outward. Any number of such ribs can be used, and two or more ribs that are parallel to each other can be particularly effective. Internal supporting ribs between the two plates can also be used. Such ribs can take the form of webs spaced apart along the top edge of the gel cavity, the bottom edge, or both, with opening between the webs to allow access to electrode buffers.

Figure 10:
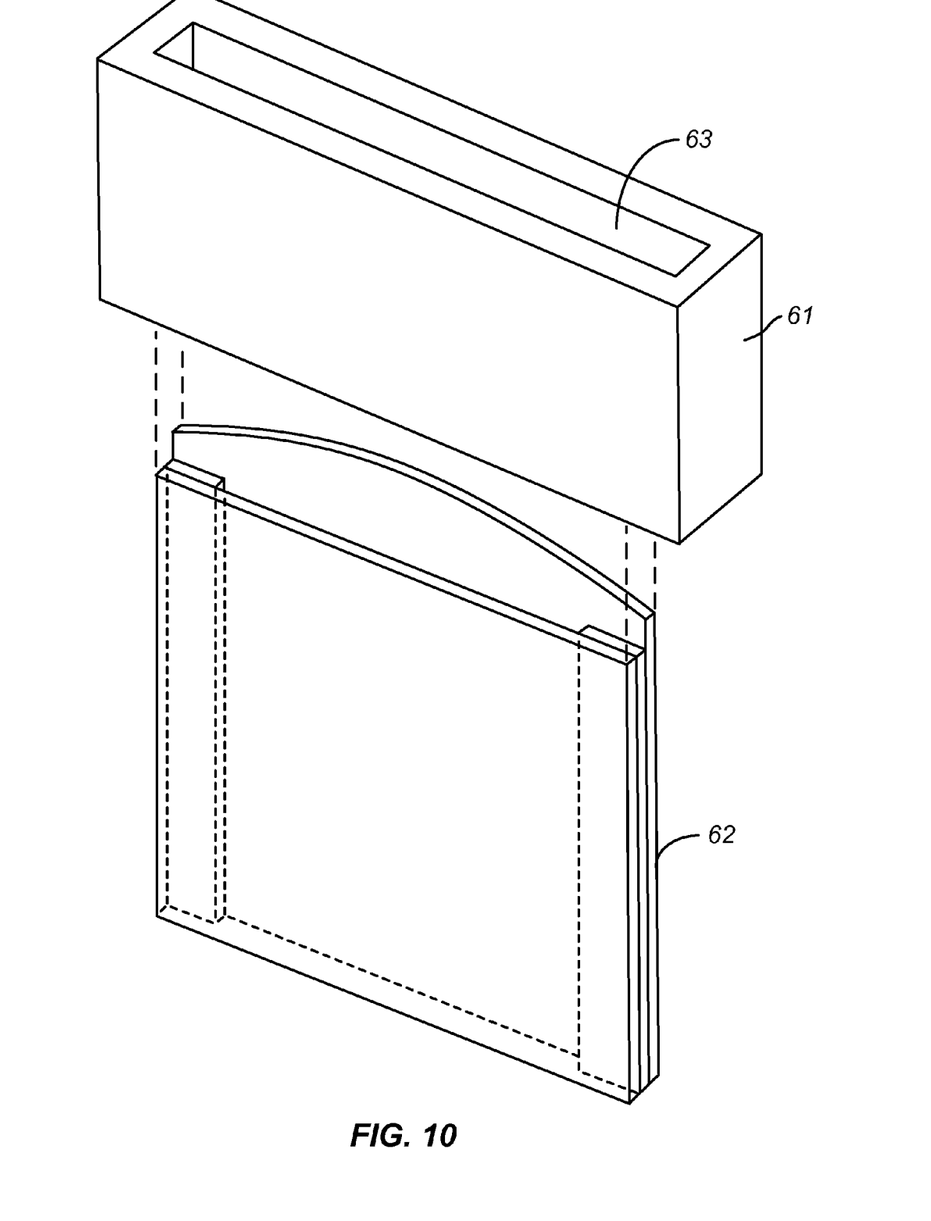
FIG. 10 is a perspective view of a combination of a slab gel cassette and an outer rigidifying enclosure, separated from each other.

Further options are those involving the use of external cages, bars, clamps, plates, and the like, that are attached to or otherwise pressed against the outer surfaces of the plastic plates that form the cassette. These external fixtures can be attached, applied, or held in place during casting of the gels, storage and shipment, or both, and removed shortly prior to use of the cassette in an electrophoresis experiment. A box, grid, or cage of rigid material such as metal, wood, or extra-thick plastic, that can be slid or otherwise placed over the cassette while contacting the outer walls of both cassette plates and readily removed prior to us of the cassette, can be used. FIG. 10 depicts such a box 61 poised above a cassette 62. The box 61 is hollow and open at the top and bottom to enable the user or manufacturer to slide the box over the cassette. The hollow center 63 of the box is long and narrow to contact the two flat plastic plates of the cassette, and the walls of the box are rigid enough to prevent any outward bowing of the flat plates of the cassette. A similar result can be achieved with a shrink-wrap type enclosure, i.e., a thick plastic film that tightly encloses the cassette after being first heated to allow the wrap to be stretched and then reheated after it is placed over the cassette to allow the wrap to return to its original unexpanded condition.

Still further options are those involving the condition in which the gel is cast and the cassette is stored. The gel can be cast in subatmospheric pressure, for example, and sealed in an air-tight enclosure while the gel is at the subatmospheric pressure. Alternatively, the gel can be cast at atmospheric pressure, then reduced in pressure to a subatmospheric pressure before sealing. In either case, sealing can be done at any time before significant swelling of the gel occurs. The cassette once sealed can then be stored in atmospheric pressure. The pressure differential between the atmospheric pressure surrounding the sealed cassette and the subatmospheric pressure inside the seal will then counterbalance any rise increase in pressure within the cassette due to swelling of the gel. The air-tight enclosure can be shrink-wrapped over the cassette. Suitable sub-atmospheric pressures are those that are about 10 psi (absolute) (69 kilopascals) or less, or from about 0.5 psi to about 10 psi (3.5 to 69 kilopascals), or from about 0.5 psi to about 5 psi (3.5 to 35 kilopascals).

Outward bowing of the plates can also be prevented at the bottom edge of the plates, i.e., the edge opposite the edge where the samples are loaded. Bowing or warping of the cassette in this region can occur for the same reasons as bowing near the top of the cassette, especially when the bottom of the cassette is open to expose the gel to a lower buffer solution. Means of reducing or eliminating bowing at or near the upper edge can also be applied to prevent bowing at or near the lower edge, with the exception of combs with hook-like projections.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A device for insertion between a pair of parallel flat casting plates to form a row of sample wells in an electrophoresis slab gel as said gel is cast between said plates, said device comprising:
    a flat bar having a forward face, a rear face, and a longitudinal edge,
    a row of dentiform projections along said longitudinal edge,
    one or more first hook(s) projecting forward from said forward face, and
    one or more second hook(s) projecting rearward from said rear face, said first and second hook(s) shaped to hold said casting plates parallel to each other and at a fixed distance from each other during expansion of the gel with said dentiform projections between said casting plates.

2. The device of claim 1 wherein one of said first hook(s) or said second hook(s) forms a row of tabs parallel to and uniformly spaced from a face of said flat bar.

3. The device of claim 1 wherein said first hook(s) forms a first row of tabs parallel to and uniformly spaced from said forward face, and said second hook(s) forms a second row of tabs parallel to and uniformly spaced from said rear face.

4. The device of claim 1 wherein, when said forward and rear faces are vertical, said second hook(s) is higher than said first hook(s).

5. A method for casting a slab gel with sample wells for electrophoresis, said method comprising:
    (a) placing a gel-forming monomer solution in a rectangular slab-shaped cavity of a gel enclosure defining said cavity with opposing upper and lower edges and opposing side edges, said gel enclosure comprising first and second flat plastic plates and one or more dividers for securing said plates together along said side edges of said cavity with a gap of preselected width between said plastic plates;
    (b) polymerizing said monomer solution to form said gel; and
    (c) before, during, or after (b), attaching the device of claim 1 to said enclosure, thereby imposing a force on said plastic plates to oppose any outward force against said plastic plates caused by pressure generated inside said cavity by a slab monomer solution or said gel.

* * * * *